(12) United States Patent  (10) Patent No.: US 6,384,382 B2
Rohner et al.  (45) Date of Patent: May 7, 2002

(54) OVEN, IN PARTICULAR FOR DENTAL MATERIAL

(75) Inventors: Gottfried Rohner, Altstatten (CH); Johannes Lorunser, Bludenz (AT); Horst Ulbricht, Eschem (LI)

(73) Assignee: Ivoclar AG, Schaan (LI)

( * ) Notice: Subject to any disclaimer, the term of this patent is extended or adjusted under 35 U.S.C. 154(b) by 0 days.

(21) Appl. No.: 09/753,991

(22) Filed: Jan. 3, 2001

Related U.S. Application Data

(60) Provisional application No. 60/204,790, filed on May 16, 2000.

(30) Foreign Application Priority Data

Feb. 24, 2000 (DE) .......................................... 100 08 603

(51) Int. Cl.[7] .............................. F27B 5/18; F27D 19/00
(52) U.S. Cl. ........................ 219/413; 219/390; 219/392
(58) Field of Search ................................ 219/413, 390, 219/385, 386, 392, 391; 374/1, 121, 187, 188

(56) References Cited

U.S. PATENT DOCUMENTS 5,331,676 A    7/1994  Lambert et al.
5,707,146 A  *  1/1998  Gaus et al. ..................... 374/1

FOREIGN PATENT DOCUMENTS

DE    41 18 032 A1      1/1993
SU      1700349 A1  * 12/1991

* cited by examiner

*Primary Examiner*—Joseph Pelham
(74) *Attorney, Agent, or Firm*—John C. Thompson; Alan S. Korman

(57) ABSTRACT

An oven particularly suitable for dental materials is provided with a firing plate on which a calibration apparatus can be removably located. The calibration apparatus includes a meltable element whose melting is detectable by a detecting device. The calibration apparatus is additionally provided with a control device. The firing plate includes a device for receiving therein the calibration apparatus including a non-electrically conducting support for supporting two electrically conducting contact posts of the calibration apparatus.

20 Claims, 4 Drawing Sheets

OVEN, IN PARTICULAR FOR DENTAL MATERIAL

This application claims benefit to 60/204,790 filed May 16, 2000.

BACKGROUND OF THE INVENTION

The present invention relates to an oven, in particular, an oven for dental material.

A so called retort oven is commonly used for the production of dental ceramic as well as for other purposes within the dental area. In this connection, a basic configuration which has shown itself to be particularly practical includes the actual heating component integrated into a liftable or swing away oven hood and comprises a substantially planar working surface having thereon corresponding markings for indicating the location at which a retort (24) for the curing of the ceramic is to be placed. This configuration permits a rapid work cycle and a minimized shaking movement of the retort (24) having the dental ceramic therein.

Retort ovens of the type just described have basically proven themselves and have been in service since easily more than a decade. However, such retort ovens must be regularly calibrated in order to assure uniform quality of the item to be fired. In this regard, a calibration program has typically been implemented. This program includes disposing a test support supporting a lengthwise extending silver wire on the curable item surface and performing a calibration sequence. An indication of a correct calibration sequence is the formation of a small, downwardly hanging bead at the end of the horizontally extending wire. A failed calibration results in either the melting of the calibration wire or an absence of melting of the wire, whereby, after an appropriate pause, a repeat of the calibration sequence must be performed. Although the melting point of gold, for example, is—at 1064.76 degrees C.—precisely ascertainable, the calibration approach just described can only yield a precision which is no more precise than within a few degrees.

Moreover, it has been suggested to wind a silver wire between two pins or posts which are disposed in sockets. An interruption of the electrical connection established through the silver wire is thus detectable upon melting of the wire. However, this approach is disadvantageous for a number of reasons. The winding does not assuredly offer the possibility of an established wire contact for the reason that the contact pressure is highly dependent upon the individually variable winding application applied by the user. There also exists the risk that oxidation will preclude establishing a reliable contact with a contact post. Additionally, a wound silver wire is prone to expansion as a result of its heating up, a result, in fact, to be expected in view of the thermal expansion coefficient of silver. It is, however, for precisely this reason that there arises the risk that such expansion will cause at, for example, 700 degrees, the breaking off of a contact which otherwise exists at room temperature. In this event, an electronic element disposed for detecting such interruptions of contact will erroneously deem such an interruption of the circuit as an indication that a desired temperature has been reached, thereby creating a significantly false calibration result.

A further disadvantage is the melting silver wire dirties the socket in which it is disposed, thereby leading to a risk of current leaking.

Yet a further disadvantage is that the cable for the calibration apparatus must be conducted to the exterior. This cable is effectively clamped, whereby it is subjected to significant stress. Moreover, it is in reality no longer possible to introduce a vacuum in the oven as the need may arise, for the reason that exterior ambient air flows interiorly along the slots of substantial length extending on both sides of the cable to such an extent that even a powerful vacuum pump cannot effect an effective reduction of the inner pressure.

Outside of the dental material oven environment, numerous other possibilities are known for calibrating an oven. For example, a calibration apparatus is disclosed in U.S. Pat. No. 5,331,676 which provides thermal elements in spaced relation to one another. It is further known, as disclosed in German patent document DE-OS 42 18 032, to provide an oven for thermal analysis, in which a test support with two thermal elements are disposed, the energization current for the thermal elements extending through the underside of the oven. The test support rests in freely movable disposition of the top surface of the underside of the oven so that the test support can, in effect, slide or slip. This calibration approach thus attempts to exploit the fact that the oven interior, although substantially wide and long, is flat.

The known approaches to calibration accordingly suffer from the significant disadvantages that an insecure and/or imprecise calibration risk is produced when such calibration approaches are implemented in connection with retort ovens.

It is one object of the present invention to provide an oven for dental material which can be calibrated in a reliable yet economical manner.

This and other objects of the present invention are achieved by an oven for dental material having the features recited in the claims herein.

SUMMARY OF THE INVENTION

The oven of the present invention comprises a firing plate, and a calibration apparatus removably locatable on the firing plate, the calibration apparatus including a meltable element which melts upon heating thereof to a predetermined temperature such that the melting of the meltable element effects a change of condition detectable by a condition change detecting device, a pair of electrically conducting elements for supporting the meltable element therebetween, and a non-electrically conducting support for supporting the pair of electrically conducting elements.

One particular advantageous configuration of the oven for dental material in accordance with the present invention includes an assembly provided as a central element on the firing plate, this assembly being covered in normal operation of the retort oven by a full covering and being uncovered for calibration. This assembly, which is preferably configured as a pan or an element having a recess, precisely establishes the position of the calibration apparatus whose outer dimensions are selected in precise correspondence with the pan or the element having a recess. In this way, it can be ensured that a false correlation or reconciliation does not result from a false placement of the calibration apparatus.

The pan permits the covered extension of the contacts which further permits the avoidance of the disadvantage that would otherwise arise from the extension of cables under an oven head. In this connection, the sealing of the oven, especially, is so configured that a vacuum operation during calibration can be implemented, if needed. This, on the other hand, opens the possibility as well that, with a view on the effect of oxidation, less critical material for the electrical conductor need only be used. No gold or platinum need be used in order to keep the calibration wire temperature stable and scale free, and thus contact secure. This makes possible, on the other hand, the use of gold calibration wire for an improved calibration, which melts at 1,064.76 degrees C. and to that extent affords an exact and improved reference.

It is also possible, through sequential use of gold and silver calibration wire, to use two calibration points, in order as well to compensate for the always necessary disadjustment of the oven in view of the temperature course and to effect the post calibration of the oven.

Through the possibility to drastically reduce the oxidation tendency by creation of a vacuum, there exists on the other hand, the possibility of configuring a reusable calibration apparatus capable of many cycles of use. In this manner, the need is eliminated to configure the calibration apparatus as a one-time use or disposable article (with the associated problems of reduced quality or, respectively, contact problems).

In accordance with the present invention, the calibration wire is preferably disposed in tension between the contact posts. In this manner, a secure contact disposition is assured and, especially, the risk is avoided that a secure contact cannot be assured due to a thermal expansion of the calibration wire. The disposition of the calibration wire in tension between the contact posts is preferably implemented by configuring the contact post as a V-shape recessed element (54) at one end thereof, in which the calibration wire is frictionally retained.

It is particularly advantageous to extend the contact connections through the floor of the oven, namely, through the stone footing, such that the contact connections are protected. In this way, it can be reliably insured that the cable is not pinched or clamped by the heavy oven hood.

In one advantageous configuration of the present invention, it is provided that contact through the stone footing is via genuinely thin wire. Such wires act as only negligible thermal bridges, at least in the operation of the pan in which they terminate, which is covered by a full plate. According to one variation, it is provided, in contrast, that the stone footing is configured with genuinely thin bores which receive therein the contact posts of the calibration apparatus upon its installation with the contact posts being received in contact springs in the bores. This configuration also permits the maintenance of a vacuum during the calibration operation.

In accordance with another variation of the calibration apparatus of the present invention, the calibration wire is omitted in lieu of a thermal element which registers a resistance change upon the achievement of a predetermined temperature which is taken into account during calibration.

In an advantageous configuration of the calibration apparatus of the present invention, the adjustment of the retort oven occurs automatically. The substantial resistance change due to, for example, the melting of the calibration wire, is captured and used as a reference temperature for the compensation of the oven.

Further details, advantages, and features are described in the following description of the several variations of the present invention in connection with the drawings.

DETAILED DESCRIPTION OF THE PREFERRED EMBODIMENTS

Figure 1:
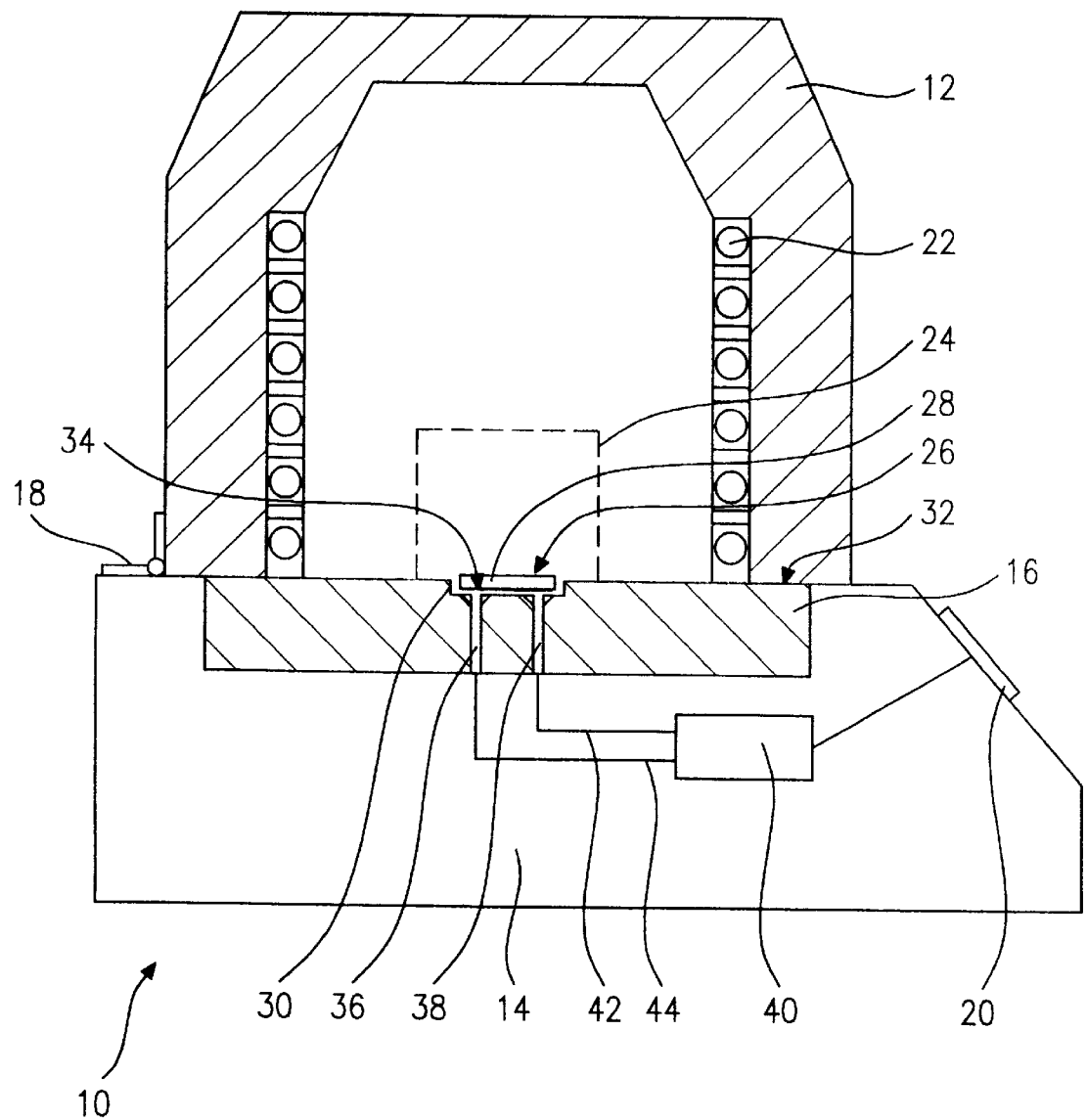
FIG. 1 is a schematic view of one embodiment of the oven of the present invention in vertical cross section.

As seen in FIG. 1, an oven 10 includes a firing hood 12 and an oven base 14, in which a firing plate 16 is integrated. The hood 12 is disposed on the oven base 14 and a hinge 18 to which the hood 12 is connected permits the hood 12 to be swung upwardly. The hinge 18 is disposed on a side of the oven base 14 opposite a side having thereon a service field 20.

Heating element 22 is integrated into the hood 12, the heating element being operable to heat as required the casing 24 (indicated by broken lines). The casing 24 is disposed on the firing plate 16 and is easily removable upon raising of the hood 12. It is to be understood that the casing 24, which is solely shown for exemplary purposes, will only be used in connection with press ovens while other curing ovens employ other firing carriers.

The firing plate 16 includes a pan 26 in which, in normal operation, a scrupulously precisely conforming full cover 28 is disposed. A small magnet or a ferromagnetic material, for example, can be integrated into the full cover 28 to thereby make it possible to raise the full cover 28 as required, in spite of its smooth top surface.

The embodiment of the oven shown in FIG. 1 has a pan and a correspondingly shaped full cover 28 which is expressly flat. It is to be understood that the configuration in other environments can be adapted thereto according to requirements. For example, the side walls 30 of the pan 26 are so configured to diverge that the full cover 28, whose shape is conformed to the pan, slides off the pan upon the application of an asymmetric pressure. Additionally, the full cover 28 can be configured of such a light weight that it sticks, for example, to a moist finger and can thus be removed. It is, however, important in any event that the non temperature varying full cover 28, at least on its top side, covers completely the pan 26 such that the firing plate 16 exhibits a closed top surface 32.

Two throughbores 36 and 38 are provided in the underside of the pan 26 which extend to the firing plate 16. The throughbores 36 and 38 serve to establish the electrical connection to the calibration apparatus which is to be operated, whereby reference is had to FIG. 2.

A schematically illustrated control apparatus is provided in the oven base 14 and is connected in a known manner to the service field 20. Connectors 42, 44 extend from the control apparatus 40 through the throughbores 36 and 38.

Figure 2:
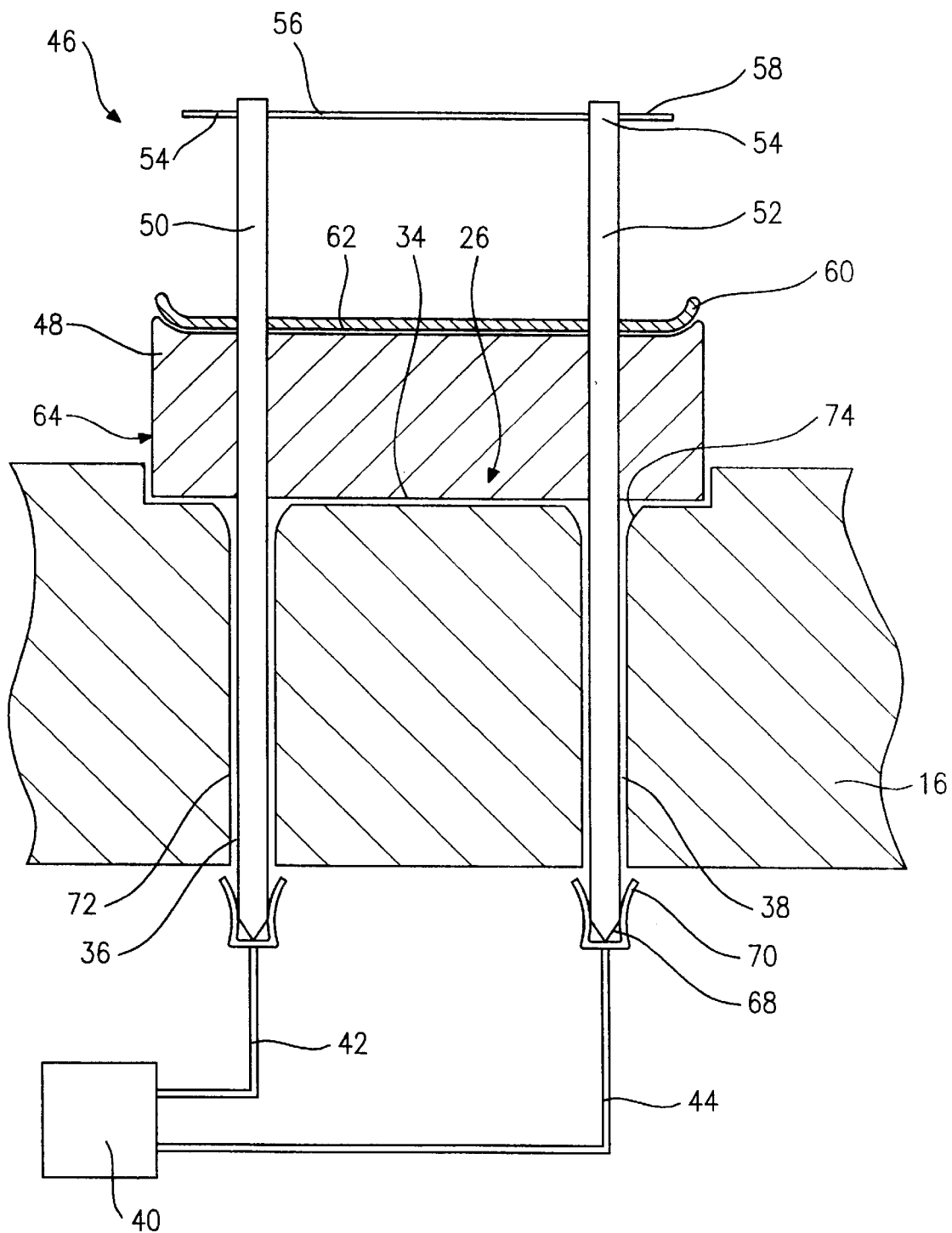
FIG. 2 is an enlarged view of the calibration apparatus of the oven shown in FIG. 1.

The variation of the calibration apparatus of the present invention shown in FIG. 2 is designated as a calibration apparatus 46. The calibration apparatus 46 includes a calibration base 48. Contact posts 50, 52 penetrate through the calibration base 48.

Each contact post 50, 52 includes a receiving element 54 at its upper end for receiving therein a meltable element in the form of a melt wire 56. The melt wire 56 extends to and beyond the upright ends 58 of the receiving element 54. Various configurations of the receiving element are viewable in FIGS. 3, 4, and 5.

The calibration apparatus 46 is provided, in the illustrated example, with a cover 60 which extends under the melt wire 56 and covers the complete top surface 62 of the calibration base 48. The cover 60 is configured as a single use article and operates to prevent contamination of the calibration base 48 by the remnants of the melted melt wire 56. For example, the cover can be comprised of a web of mineral wool or mineral wool fibers which is inserted past the posts 50, 52 before the melt wire 56 is clamped into position.

The calibration base 48 is configured as a ceramic body and includes side surfaces 64 which act as hand grips. The top side 62 is formed with a slight trough shape such that the falling off of melt wire remnants is rendered less likely. In this connection, these measures act to improve the function of the side surfaces 64 as hand grips.

The contact posts 50, 52 comprise, at their lower ends, a conical portion 68 which acts as an insertion aid for insertion of the post into friction fit elements 70. The friction fit elements 70 are fixedly mounted to the oven. The friction fit elements 70 comprise spring contacts which ensure a secure contact of the electrically conducting posts 50, 52. Additionally, the friction fit elements 70 are connected to wires 42, 44.

The calibration apparatus 46 including the wires is configured as a temperature stable and oxidation stable configuration. It is also substantially small; for example, the cross section of the calibration base 48 comprises approximately 10 mm. The contact posts 50, 52 can, for example, be configured as steel posts and can be formed of two portions, whereby the upper portion, which is subjected to oxidation, can be replaced as needed. In connection with use of the oven without vacuum, it is advantageous if the contact posts are comprised of platinum and that the friction fit elements 70 are formed of gold or are gold plated whereby, in the area of the firing plate 16, the temperature is substantially lower. Silver wire is suitable for the wires 42, 44, whereby it is to be understood that the choice of material can be chosen in many environments in correspondence with the requirements of such environments.

If the calibration apparatus is to be operated exclusively in a vacuum condition—which is possible in accordance with the present invention—it is also possible to use a suitable steel for the contact posts 50, 52, whereby, with respect to the absence of oxygen or only a relatively very small concentration of oxygen, no oxidation need be feared. It is to be understood that the calibration program, which is controlled by the control apparatus 40, firmly dictates the corresponding parameters as are necessary to foreclose a fault control instruction.

To perform a calibration of the oven, the calibration base 48 initially receives the contact posts 50, 52 after the full cover 28 has been removed. In this regard, the user grips the calibration apparatus 46 uniformly on the side surfaces 64—not gripping the contact posts 50, 52—and disposes the conical portions 68 of the contact posts in the friction fit elements 70. In this connection, the insertion tapers 74, which are formed at the open end of the bores 72, assist in the insertion of the contact posts.

Thereafter, the cover web 60 is inserted past the contact posts 50, 52. Then, the calibration wire in the form of the melt wire 56 is symmetrical disposed on the contact posts 50, 52. In this regard, the user grips the two upright ends 58 and lightly pulls the calibration wire into the receiving element 54.

The firing hood 12 is thereafter lowered and the service field 20 effects the starting of the calibration program. The control device 40 detects the drastically increased electrical resistance between the conductors 42, 44 which occurs upon the melting of the melt wire 56 and uses the contemporaneous temperature as a reference temperature for internal comparison and compensation of the oven.

In accordance with the present invention, it is possible, for example, to use two reference points whereby one calibration program is performed using a gold melt wire and a second calibration program is performed using a silver melt wire. In this manner, two reference temperatures—namely, 1,064.76 degrees C. for gold and 961.3 degrees C. for silver—are used as reliable calibration temperatures so that a curve comparison of temperature curves of the oven would be possible.

Figure 3:
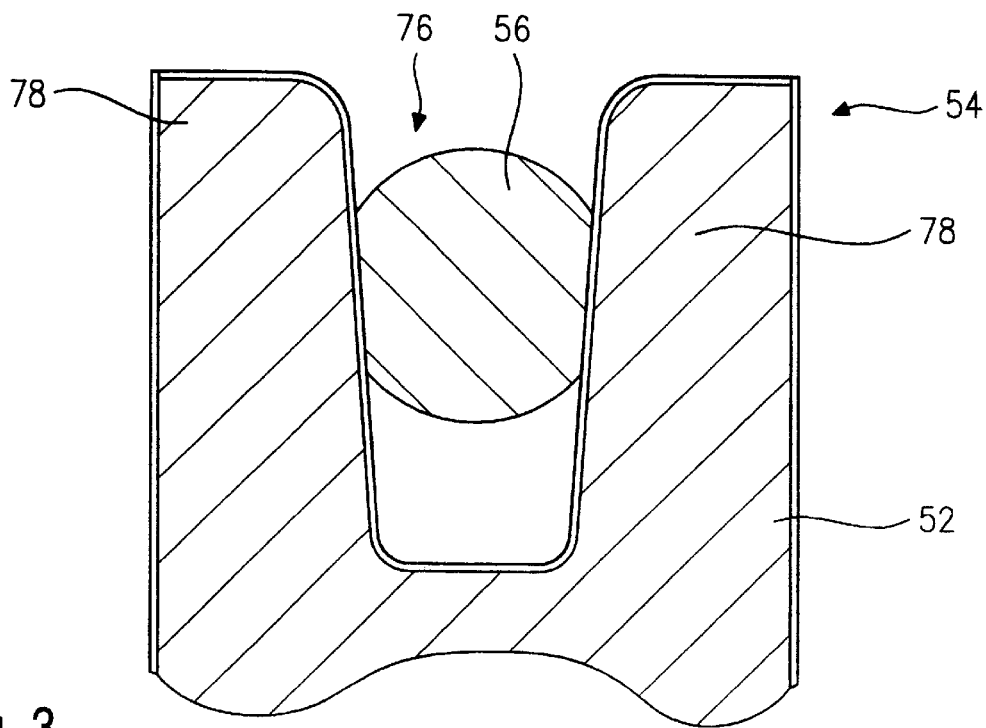
FIG. 3 is an enlarged view of the contact post of the calibration apparatus shown in FIG. 2.

Another possible variation of the receiving portion 54 of a contact post 50, 52 is shown in FIG. 3. In this variation, the receiving portion 54 comprises a substantially U-shaped slot 76 whose large side prongs 78 diverge slightly outwardly and upwardly. The divergence angle comprises in the illustrated variation 10 degrees. The side prongs of a slot of such construction are resiliently slightly deformed upon insertion of the melt wire 56 into the slot, whereby the divergence angle is so minimal that the friction against the wire is sufficient to prevent the melt wire 56 from being pushed upwardly. In this manner, a secure contact is possible through simple means.

Figure 4:
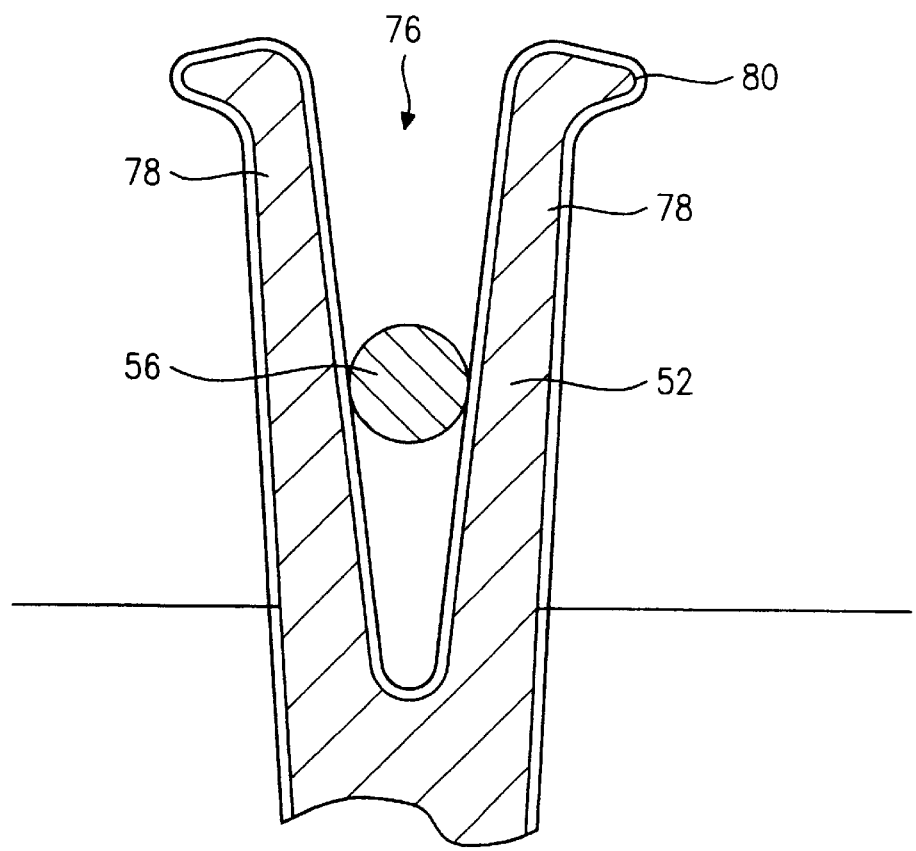
FIG. 4 is an enlarged view of a further configuration of a contact post of a calibration apparatus of the present invention.

A modified configuration of a contact post 52 is shown in FIG. 4. In this configuration, the contact post 52 is comprised substantially of quartz which is tempered with platinum. The slot 76 is in this configuration substantially deeper so that a shape retaining or memory property exists and the side prongs 78 are displaced outwardly relative to one another upon insertion of the melt wire 56 into the slot. Furthermore, this configuration produces a secure contact between the platinum coating 80 and the melt wire 56.

Figure 5:
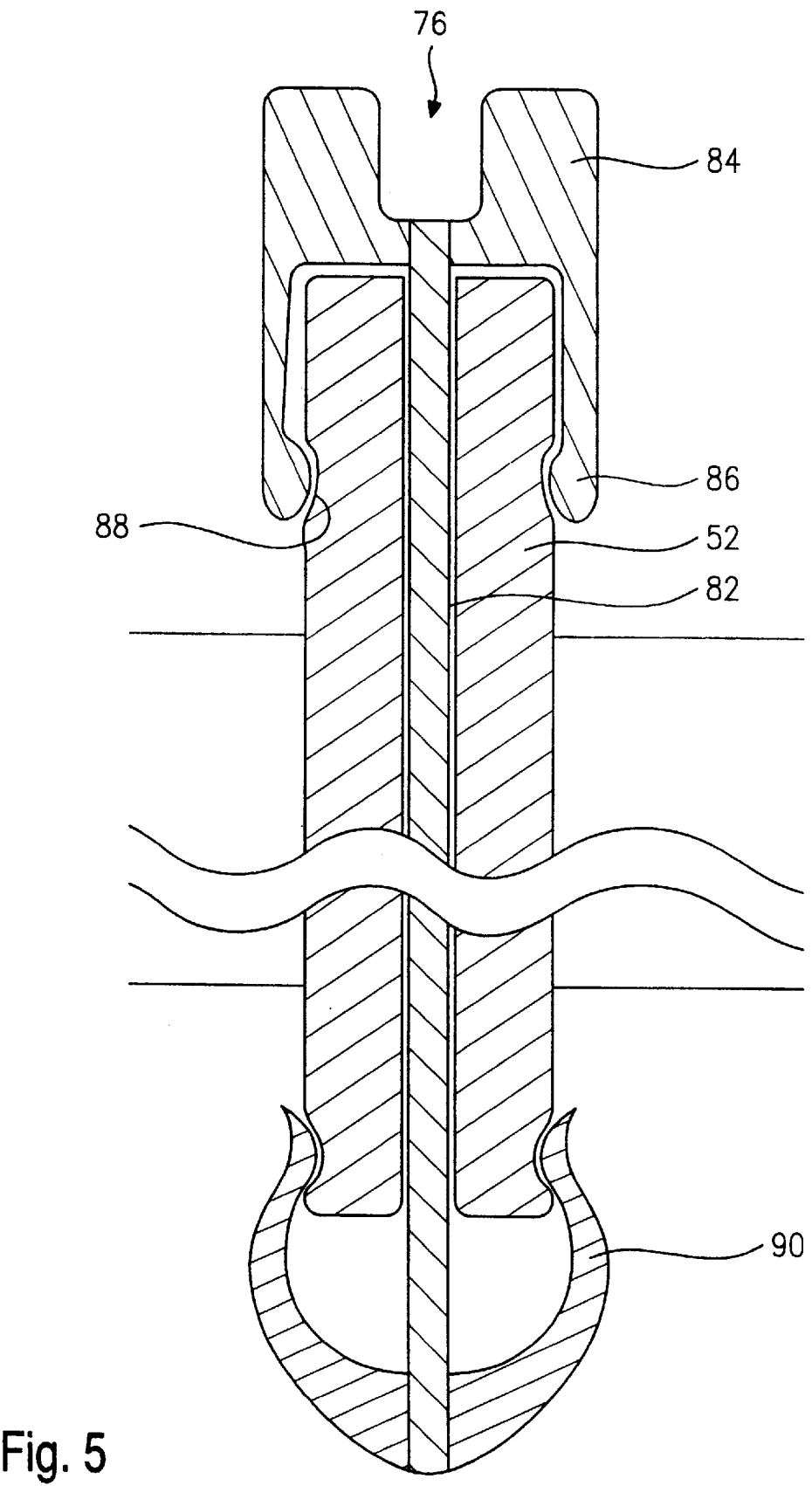
FIG. 5 is an enlarged view of yet another configuration of a contact post of a calibration apparatus of the present invention.

Yet another modified configuration is shown in FIG. 5. In this configuration, the contact post 52 is comprised of quartz glass. The contact post includes a throughbore 82 through which a thin wire extends. A contact cap 84 forms the slot 76 for the receipt therein of a melt wire (not shown). The contact cap 84 includes grip flanges 86 which engage side recesses 88 formed in the contact post 52. The contact cap 84 is interiorly and exteriorly wrapped with platinum wire.

A different contact cap 90 is likewise wrapped with platinum wire and frictionally engages the lower end of the contact post 52. The contact cap 90 is compatibly configured with the open introduction end of the friction fit elements 70. This contact cap configuration permits the configuring of a contact post 52 with relatively less platinum material, whereby it is to be understood that this contact cap configuration is generally most suitable if the total calibration apparatus is substantially larger than has been described heretofore.

Other variations of the calibration apparatus of the present invention are also possible. For example, each contact post 50, 52 can be inserted fully through the throughbores 36, 38, which permits the friction fit elements 70 to be located below the firing plate 16. This configuration permits the construction of each contact post 50, 52 as a two piece assembly with the upper portion thereof operable as the test element support and the lower portion thereof configured with threads for threaded mounting engagement. Particular attention should be paid with this configuration that side pressure on the contact post upper or lower portions does not break the calibration base 48.

Additionally, the calibration base 48 can be shaped as desired. For example, the socket can be oval, annular or right angled. It is in any event preferable to select the size of the socket such that it is ensured that no remnants of the meltable wire 56 can dirty the firing plate 16.

The present invention is, of course, in no way restricted to the specific disclosure of the specification and drawings, but also encompasses any modifications within the scope of the appended claims.

What we claim is:

1. An oven operable to fire dental material, comprising:
   a firing plate; and
   a calibration apparatus removably locatable on the firing plate, the calibration apparatus including a meltable element which melts upon heating thereof to a predetermined temperature such that the melting of the meltable element effects a change of condition detectable by a condition change detecting device, a pair of electrically conducting elements for supporting the meltable element therebetween, and a non-electrically conducting support for supporting the pair of electrically conducting elements.

2. An oven according to claim 1 wherein the calibration apparatus is receivable in a pan formed in the firing plate.

3. An oven according to claim 1 wherein the meltable element is tensionable between the pair of electrically conducting elements and further comprising a pair of friction fit retaining components for retaining therein lower ends of the electrically conducting elements in a friction fit manner.

4. An oven according to claim 2 wherein the non-electrically conducting support is placeable in the pan and further comprising a cover for covering the pan during oven operation.

5. An oven according to claim 1 wherein each electrically conducting element includes a receiving portion for receiving an end portion of the meltable element so as to establish a secure electrical contact between the electrically conducting element and the meltable element.

6. An oven according to claim 5 wherein the meltable element is in the form of a wire and the receiving portion of each electrically conducting element compressively engages a respective end portion of the wire.

7. An oven according to claim 5 wherein the receiving portion of each electrically conducting element is in the form of an open end slot.

8. An oven according to claim 1 and further comprising a pair of spring retaining components for retaining therein lower ends of the electrically conducting elements.

9. An oven according to claim 8 wherein the firing plate includes throughbores for receiving the contact posts therein, the diameter of each throughbore being only slightly larger than the diameter of a contact post and having an insertion taper at the open entrance end thereof.

10. An oven according to claim 2 wherein the non-electrically conducting support comprises a substantially temperature insensitive material whose thermal expansion coefficient is substantially at least as large as the thermal expansion coefficient of the material comprising the contact posts.

11. An oven according to claim 10 wherein the non-electrically conducting support comprises ceramic material and includes side surfaces extending upwardly relative to the sides of the pan and which are operable as hand grips.

12. An oven according to claim 1 wherein the meltable element is a wire having a thickness selected to be relatively less than the cross width between the opposed sides of the receiving portion of the contact posts, the wire being compressively retainable between the opposed sides of the receiving portion of the contact posts.

13. An oven according to claim 5 wherein the meltable element has an extent greater than the spacing between the pair of electrically conducting elements such that each opposed end portion of the meltable element extends outwardly beyond a respective one of the electrically conducting elements such that the end portion is operable as a hand grip for positioning the meltable element in the receiving portion of the respective electrically conducting element.

14. An oven according to claim 1 wherein the meltable element is comprised of a material having a melting point within a relatively narrow temperature range.

15. An oven according to claim 1 and further comprising a cover for covering the non-electrically conducting support, the cover being insertable over the contact posts onto its covering disposition the non-electrically conducting support for catching thereupon the melted remnants of the meltable element upon its melting.

16. An oven according to claim 15 wherein the cover is comprised of a substantially temperature insensitive material in the form of a selected one of quartz glass fiber or mineral wool fiber.

17. An oven according to claim 1 wherein the contact posts are comprised of a material at least substantially resistant to oxidation at high temperatures.

18. An oven according to claim 2 and further comprising a cover for at least substantially covering the pan.

19. An oven according to claim 1 and further comprising a control device coupled to the calibration apparatus operable to capture the occurrence of a melting of the meltable element in connection with a calibration of the oven.

20. A calibration apparatus for calibrating an oven, the oven having a firing plate, the calibration apparatus comprising:
   a meltable element which melts upon heating thereof to a predetermined temperature such that the melting of the meltable element effects a change of condition detectable by a condition change detecting device;
   a pair of electrically conducting elements for supporting the meltable element therebetween; and
   a non-electrically conducting support for supporting the pair of electrically conducting elements.

* * * * *